United States Patent [19]

Smith et al.

[11] Patent Number: 4,615,224
[45] Date of Patent: Oct. 7, 1986

[54] AIR SAMPLING SYSTEM FOR SMOKE DETECTION

[75] Inventors: Grant M. Smith, Bryn Athyn; Samuel R. Romania, Phoenixville; Vladimir M. Tamarkin, Philadelphia, all of Pa.

[73] Assignee: Burroughs Corporation, Detroit, Mich.

[21] Appl. No.: 764,230

[22] Filed: Aug. 9, 1985

[51] Int. Cl.⁴ ............................................. G01N 1/26
[52] U.S. Cl. ................................................. 73/863.33
[58] Field of Search ........... 73/863.31, 863.33, 863.51, 73/863.01, 864.73, 864.34; 340/627, 628, 629

[56] References Cited

U.S. PATENT DOCUMENTS

| | | | |
|---|---|---|---|
| 2,687,185 | 8/1954 | McChesney | 73/863.51 |
| 2,930,237 | 3/1960 | Fowle, Jr. et al. | 73/864.34 |
| 3,357,257 | 12/1967 | Herndon et al. | 73/863.33 |
| 3,427,880 | 2/1969 | Grobel et al. | 340/627 |
| 3,511,099 | 5/1970 | Harsha | 73/863.51 |
| 3,774,044 | 11/1973 | Langeron | 340/627 |
| 4,208,655 | 6/1980 | Phillips | 340/627 |
| 4,254,414 | 3/1981 | Street et al. | 340/627 |

Primary Examiner—Stewart J. Levy
Assistant Examiner—Robert R. Raevis
Attorney, Agent, or Firm—Francis A. Varallo; Mervyn L. Young; Kevin R. Peterson

[57] ABSTRACT

The present disclosure describes an air sampling system which is particularly effective in detecting minute quantities of smoke caused by electrical short circuits in equipment housed in an air cooled cabinet. More, specifically, the system is useful where large number of rack-mounted printed circuit cards are employed. The system employs air sampling cylinders mounted in proximity to the cards, and through the establishment of a pressure differential, causes an air sample to be drawn into the tubes and through a detector box which includes a smoke detection unit. The presence of smoke is conveyed to a control box which responds by removing electrical power to the cards, thereby averting further damage to the cards or surrounding structures.

9 Claims, 5 Drawing Figures

AIR SAMPLING SYSTEM FOR SMOKE DETECTION

BACKGROUND OF THE INVENTION

The development of more powerful and sophisticated electronic equipment, such as that comprising a computer system, involves an ever increasing circuit package density. The combination of smaller physical size and increased power requirements results in complex multilayer printed circuit boards or cards. Concomitant with such complexity, there exists the increased probability of defects. Although most defects present in the cards themselves, or in the components disposed thereon, are detected at an early stage by routine inspection procedures, some latent defects escape detection. Therefore, it is possible for defective cards to be assembled and installed in the computer system.

After the system has been operating for some time, the aforementioned latent defects may surface, often with serious consequences. For example, a short circuit may develop between power planes in the respective layers of a card. The large amount of current flowing in such planes as a result of the short circuit causes a tremendous amount of heat to be generated within a small area. Since it is common for computer systems to operate for many hours at a site which is untended, the heat generated by the short circuit could destroy not only the card, but unless power is quickly removed from the equipment, could pose a threat of fire to the entire system and to the surrounding structures.

In practice, a large number of cards are mounted in close, parallel, spaced-apart relationship in a card rack disposed in a cabinet. The rack is air cooled by a blower located at the bottom of the cabinet. High velocity air is directed between the cards and exits the upper part of the cabinet. Although the cards are formed of material which will not support combustion and hence, are self extinguishing, heat from a short circuit, either within the card or in the components, will generate a small quantity of smoke. The latter is difficult to detect by a conventional smoke detector unit mounted in the top of the cabinet because of the card configuration and the dissipation of the smoke by the large volume of cooling air exiting the cabinet.

What is needed is an air sampling system which is highly responsive to smoke generated by short circuits in the cards and components or in the backplane wiring which interconnects the cards. Such a system must be reliable and effective at an early stage of the malfunction, and be capable of automatically shutting off electrical power to the card rack. Additionally, from a mechanical standpoint, the system should be universal. That is, the system components should be capable of being installed with little if any modification, in cabinets of various sizes and internal configurations. The smoke detection system of the present invention meets the foregoing requirements.

SUMMARY OF THE INVENTION

In accordance with the present invention, there is provided an air sampling system for detecting the presence of smoke in a cabinet for housing electronic equipment. The system finds particular application in an air-cooled enclosure having one or more card racks, each containing a plurality of circuit cards.

In an actual operative environment, the present system includes a plurality of parallel, spaced-apart air sampling tubes situated in proximal, transverse relationship to the card edges which are downstream from the blower source of cooling air. At least one additional sampling tube, lying in the same plane as the aforementioned tubes, is positioned over the backplane area. The tubes are each closed at one extremity thereof, and open into a common manifold at their opposite extremities. Small taps or holes are formed in the tubes, and are oriented such that a static pressure on the surface of the tubes is achieved.

Detector apparatus comprised of a dual-chamber detector box and a smoke detection unit is provided. One of the chambers may be characterized as being "high pressure"; the other, "low pressure". The high pressure chamber is coupled via an air-tight connection to the sampling manifold. The low pressure chamber is connected to a draft tube situated in the low pressure area of the card rack enclosure—such low pressure resulting from the suction of the cooling blower. The low pressure environment causes some of the air which has passed over the planar surfaces of the cards, or is present in the backplane area, to enter the sampling tubes and to be drawn into the detector box where it is examined by the smoke detection unit. The latter unit is adapted to actuate a relay in response to the presence of smoke in the air sample, and thereby to remove electrical power from the card racks. Once power has been removed, the danger of completely destroying a card or causing a fire is eliminated.

Other features and advantages of the present invention will become apparent in the detailed description thereof which follows.

DETAILED DESCRIPTION OF THE PREFERRED EMBODIMENT

Figure 1:
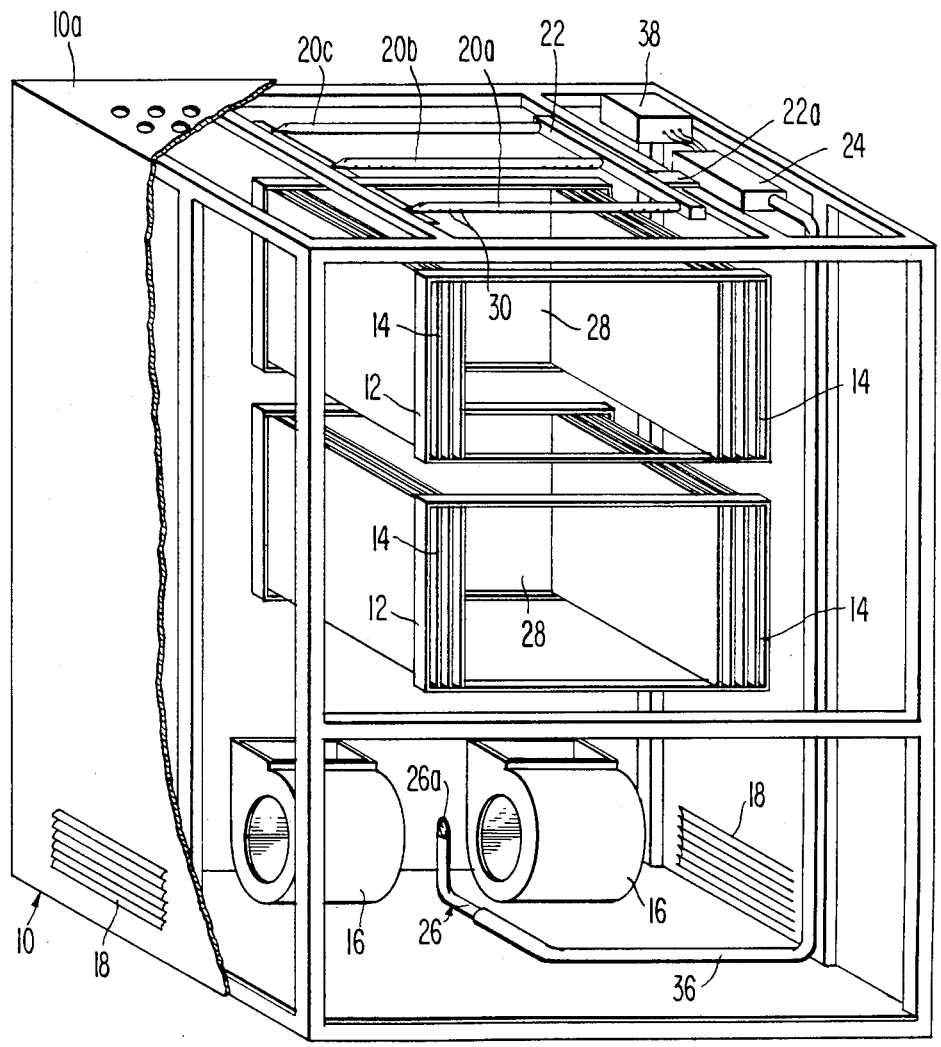
FIG. 1 illustrates in simplified form, the air sampling system of the present invention installed in a typical air-cooled cabinet having a plurality of circuit cards.

FIG. 1 depicts an actual working environment for the air sampling system of the present invention. A cabinet 10 is shown with its exterior walls partially cut away to illustrate a pair of card racks 12, each containing a plurality of printed circuit boards or cards 14. A pair of blower scrolls 16, driven by a motor (not shown) and located at the bottom of cabinet 10, draw surrounding air into the cabinet, such as through louvers 18. Accordingly, a large volume, fast moving, air stream is directed by the scrolls over the planar surfaces of the cards which lie parallel to the direction of air flow. The air stream then exits the perforated top 10a of the cabinet.

Figure 2:
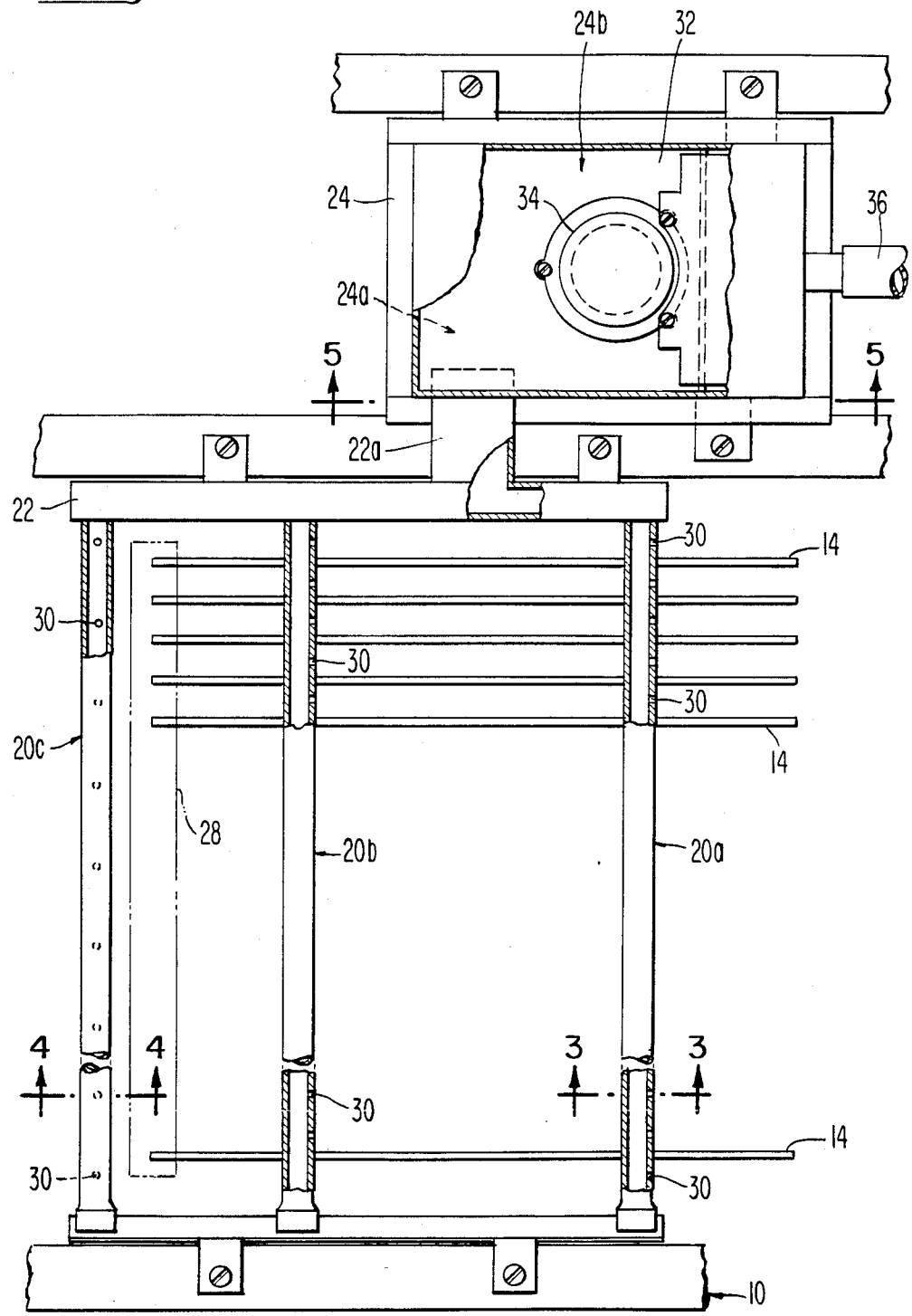
FIG. 2 is a plan view of the air sampling system of FIG. 1.

With continued general reference to FIG. 1 and more specific reference to FIG. 2, the air sampling system of the present invention is seen to be comprised of a plurality of cylindrical air sampling tubes 20a, 20b and 20c, a common manifold 22, a detector box 24, and a draft tube 26. More particularly, the air sampling tubes 20a, 20b and 20c are oriented normal to the direction of the cooling air stream. Two of the sampling tubes, namely 20a and 20b, are positioned in proximity to the edges of cards 14 and are adapted to sample the air which has passed over the cards in order to detect the presence of smoke. One of the sampling tubes 20c monitors the area adjacent the backplane 28 for the presence of smoke from the interconnect wiring.

The sampling tubes 20a, 20b and 20c are closed at one extremity thereof, and have a number of taps or holes 30 formed therein. As will be discussed hereinafter in connection with FIG. 3, the holes 30 are oriented such that a static pressure condition is maintained on the sampling tubes 20a and 20b. The opposite extremities of tubes 20a, 20b and 20c open into a common sampling manifold 22.

As seen in FIG. 2, (and in the section view of FIG. 5), the detector box 24 comprises dual chambers 24a and 24b formed by hood 32 which also supports a smoke detection unit 34 interposed between the last mentioned chambers. The sampling manifold 22 of FIG. 2 includes an integral projection 22a which provides an air tight connection to the high pressure chamber 24a of box 24. The low pressure chamber 24b is coupled by a flexible hose 36 to the draft tube 26 located in the bottom of the cabinet 10. Such location is a low pressure area created by the suction of the blower scrolls 16. The pressure differential in the air sampling system is maximized by virtue of a further decrease in pressure in draft tube 26 effected by suction air flowing past the angled or obliquely cut top or extremity 26a thereof.

Figure 3:
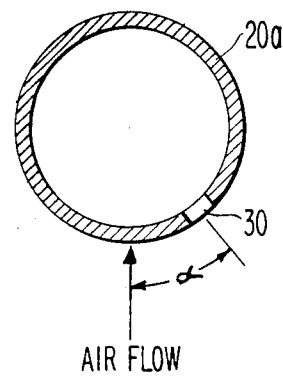
FIG. 3 is a section view taken along lines 3—3 of FIG. 2 and illustrating the placement of the holes in an air sampling tube positioned over the card rack.
Figure 4:
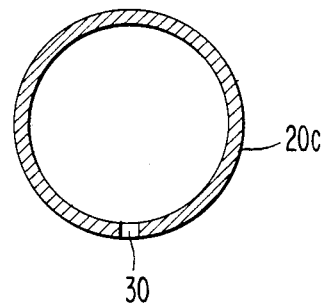
FIG. 4 is a section view taken along lines 4—4 of FIG. 2 and illustrating the placement of the holes in an air sampling tube positioned over the backplane wiring.

With reference to FIG. 3, which shows the orientation of the holes 30 in the sampling tube 20a (the holes in tube 20b having an identical orientation), it is known that a static pressure occurs on the surface of the tube 20a as a result of the attainment of the "critical angle", α. The latter is defined by the arcuate distance on the surface of the tubes, between the direction of air flow indicated by the arrow and the location of the tap or hole 30. Variations in the critical angle occur as a result of changes in the velocity of the air stream, and the ratio of the diameter of the hole 30 to the diameter of the tube 20a. As to sampling tube 20c, shown in FIG. 4, which is positioned over the backplane wiring area 28 and is not in the blower airstream, the surface of the tube is at an ambient or static pressure and the critical angle criterion does not apply. Accordingly, the holes 30 in the surface of tube 20c are shown in FIGS. 2 and 4 as being oriented directly downward toward the wiring in order to detect any traces of smoke but may be oriented otherwise without change in performance. Thus, the respective surfaces of all of the sampling tubes 20a, 20b and 20c are at substantially the same pressure, namely static pressure, and the sampling system is balanced.

Figure 5:
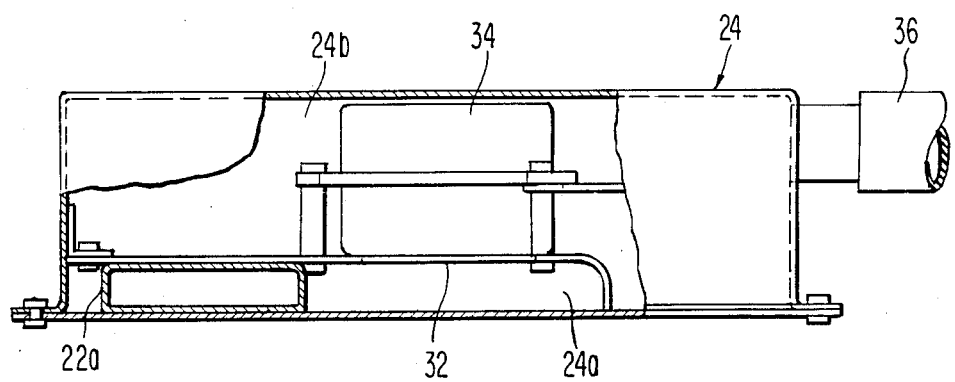
FIG. 5 is a section view taken along lines 5—5 of FIG. 2, with portions cut away to illustrate the detector box with its dual chamber configuration and a smoke detection unit interposed between the chambers.

The air sampling system of the present invention operates as follows. With reference to FIGS. 1 and 2, if a short circuit develops on a card 14 or in the backplane area 28, the heat generated thereby will cause the electrical insulation to burn, creating smoke. The smoke mixes with the cooling air supplied by the blower scrolls 16 and exits the perforated top 10a of the cabinet 10. A portion of this air/smoke mixture will be drawn into the holes 30 in the air sampling tubes 20a, 20b and 20c as a result of the pressure differential created by the system. The air sample passes through the manifold 22 and enters the high pressure chamber 24a of the detector box 24 (as also seen in FIG. 5). From there, the air sample passes via an opening in hood 32, through the smoke detection unit 34 and enters the low pressure chamber 24b of the detector box 24. When the smoke detection unit 34 senses smoke in the air sample, it actuates a relay in a power control box 38 to which it is electrically coupled, causing power to be removed from the card racks 12. Since none of the material used in the equipment within the cabinet will support combustion, removal of the electrical power from the cards 14 will permit the fire to self extinguish.

In actual operative embodiments of the present invention, the cylindrical air sampling tubes 20a, 20b and 20c are approximately 25 inches in length, have an outside diameter of 0.7 inches and a wall thickness of 0.035 inches. Tubes 20a and 20b each have 23 equally spaced, like-oriented taps or holes 30, approximately 0.102 inches in diameter. Tube 20c has 12 equally spaced holes, approximately 0.076 inches in diameter. Assuming that the blower scrolls 16 provide air flow at 2000 c.f.m., the critical angle, for tubes 20a and 20b is approximately 40°. The smoke detection unit 34 is of the ionizing type, manufactured by Statitrol, Inc. of Lakewood, Colo. and identified as Model 306 MO. It should be understood that the foregoing data has been provided solely for purposes of example and should not be construed as limitative of the invention.

In conclusion, there has been described an effective system for dealing with circuit malfunctions which result in overheating and the generation of small quantities of smoke, intermixed with a large volume of cooling air. It is apparent that depending upon the particular application, changes and modification of the system as described herein may be required. Such changes and modifications, insofar as they are not departures from the true scope of the invention, are intended to be covered by the claims which follow:

What is claimed is:

1. An air sampling system for diposition in a cabinet having a source of cooling air, for detecting the presence of smoke in cooling air directed over the planar surfaces of a plurality of printed circuit cards interconnected in a backplane, comprising:

at least a first air sampling tube oriented normal to the direction of flow of said cooling air, said first air sampling tube being positioned in proximal, transverse relation to the edges of said cards, said last mentioned edges being those farthest removed from said source of cooling air, said first air sampling tube being closed at one extremity thereof and open at its opposite extremity, said first air sampling tube having a plurality of spaced-apart holes of predetermined orientation formed therein along its length, at least a second air sampling tube arranged in coplanar, spaced-apart relationship with said first air sampling tube and being positioned outside the flow of said cooling air and in a proximal, parallel relationship to said backplane, said second air sampling tube being closed at one extremity thereof and open at its opposite extremity, said second air sampling tube having a plurality of spaced-apart holes formed therein along its length, a detector box comprising first and second chambers, a smoke detection unit interposed between said chambers, a manifold having a plurality of input ports and an output port, the open extremities of at least said first and second air sampling tubes being connected respectively to a pair of said input ports, said output port being connected to said first chamber of said detector box, said predetermined orientation of said holes formed in said first sampling tube effecting a pressure on the surface of said last mentioned tube which is substantially the same as that on the surface of said second air sampling tube, whereby the respective pressures on said first and second tubes are balanced, a draft tube located in a low pressure area of said cabinet as effected by said source of cooling air, means coupling said draft tube to the second chamber of said detector box, whereby the pressure differential present between said first and second air sampling tubes and said second chamber of said detector box causes a Plurality of air samples to be drawn into said last mentioned air sampling tubes and through said smoke detection unit.

2. An air sampling system as defined in claim 1 characterized in that at least a third air sampling tube arranged in coplanar, spaced-apart relationship with said first and second air sampling tubes is positioned in proximal, transverse relation to said edges of said cards, said third air sampling tube being closed at one extremity thereof and open at its opposite extremity, said third air sampling tube having a plurality of spaced-apart holes formed therein along its length and of like predetermined orientation as the holes formed in said first air sampling tube, the open extremity of said third air sampling tube being connected to a third of said plurality of input ports of said manifold.

3. An air sampling system as defined in claim 3 wherein said first, second and third air sampling tubes are cylindrical in form.

4. An air sampling system as defined in claim 3 wherein said second air sampling tube is at static pressure and said predetermined orientation of said holes in said first and third air sampling tubes corresponds to the critical angle at which said static pressure is effected on the surface of said last mentioned tubes.

5. An air sampling system as defined in claim 4 wherein said predetermined orientation of said holes in said second air sampling tube is such that the holes are disposed on the periphery of the tube closest to said backplane.

6. An air sampling system as defined in claim 5 further characterized in that said first and second chambers of said detector box are formed by a hood disposed within said box and dividing the latter into said chambers, said hood supporting said smoke detection unit and having an opening formed therein, whereby air drawn into said first chamber passes via said last mentioned opening in said hood, through said detection unit into said second chamber.

7. An air sampling system as defined in claim 6 wherein the tip of said draft tube situated in the low pressure area created by the suction of said source of cooling air is cut obliquely to further lower the pressure in the draft tube in response to suction air flowing thereover and thereby to effect a maximum pressure differential in said system.

8. An air sampling system as defined in claim 7 wherein said draft tube is coupled to said second chamber of said detector box by a flexible hose.

9. An air sampling system as defined in claim 8 further including a control box electrically coupled to said dectector box, whereby the presence of smoke causes said control box to remove power from said cards.

* * * * *

UNITED STATES PATENT AND TRADEMARK OFFICE
CERTIFICATE OF CORRECTION

PATENT NO. : 4,615,224
DATED : October 7, 1986
INVENTOR(S) : Grant M. Smith, et al.

It is certified that error appears in the above-identified patent and that said Letters Patent are hereby corrected as shown below:

Claim 1, Col. 4, line 41, change "diposition" to --disposition--.
Claim 1, Col. 5, line 22, change "Plurality" to --plurality--.
Claim 3, Col. 6, line 1, change "claim 3" to --claim 2--.

Signed and Sealed this

Sixteenth Day of December, 1986

*Attest:*

DONALD J. QUIGG

*Attesting Officer*   *Commissioner of Patents and Trademarks*